United States Patent [19]

Toth

[11] Patent Number: 5,055,395
[45] Date of Patent: Oct. 8, 1991

[54] LATEX AGGLUTINATION METHOD FOR THE DETECTION OF ANTI-STREPTOCOCCAL DEOXYRIBONUCLEASE B

[75] Inventor: Tibor Toth, Marburg, Fed. Rep. of Germany

[73] Assignee: Behringwerke Aktiengesellschaft, Fed. Rep. of Germany

[21] Appl. No.: 114,868

[22] Filed: Oct. 30, 1987

[30] Foreign Application Priority Data

Nov. 3, 1986 [DE] Fed. Rep. of Germany ....... 3637253

[51] Int. Cl.$^5$ .......................................... G01N 33/533
[52] U.S. Cl. .................................... 435/7.33; 435/7.4; 435/7.92; 435/18; 435/184; 435/188; 435/196; 435/970; 436/533; 436/534; 436/535; 436/823; 436/808
[58] Field of Search .................... 435/7, 188, 196, 810, 435/184, 18, 69, 7.33, 7.4, 7.92; 436/533, 534, 535, 823, 808

[56] References Cited

U.S. PATENT DOCUMENTS

| | | | |
|---|---|---|---|
| 3,057,782 | 10/1962 | Lindner et al. | 167/78 |
| 4,264,766 | 4/1981 | Fischer | 436/533 X |
| 4,381,921 | 5/1983 | Pierce et al. | 436/531 |
| 4,464,468 | 8/1984 | Avrameas et al. | 435/179 |
| 4,703,107 | 10/1987 | Monsigny et al. | 530/331 |
| 4,734,362 | 3/1988 | Hung et al. | 435/68 |

FOREIGN PATENT DOCUMENTS 224463 6/1987 European Pat. Off. ............. 435/18

OTHER PUBLICATIONS

Heath-Fracica et al, Diag. Microbiol. Infect. Dis 8(1), 1987, 25-30.

E. L. Kaplan et al., "The Influence of the Site of Infection on the Immune Response to Group A Streptococci", The Journal of Clinical Investigation, 49:1405-1414 (1970).

Primary Examiner—Esther L. Kepplinger
Assistant Examiner—Carol A. Spiegel
Attorney, Agent, or Firm—Finnegan, Henderson, Farabow, Garrett, and Dunner

[57] ABSTRACT

An agglutination method for the detection of antibodies against streptococcal deoxyribonuclease B is described, in which carrier-bound antibodies against streptococcal DNase B are mixed with a solution of streptococcal DNase which contains a protease inhibitor, and the sample in which the antibodies are to be detected, as well as an agent suitable for this method.

11 Claims, No Drawings

LATEX AGGLUTINATION METHOD FOR THE DETECTION OF ANTI-STREPTOCOCCAL DEOXYRIBONUCLEASE B

The invention relates to a stabilized solution of streptococcal DNase B and to its use in an agglutination method for the detection of antibodies against streptococcal DNase B.

Streptococcal DNase is an extracellular metabolite of Lancefield Streptococci A. Group A Streptococci produce four different deoxyribonucleases (streptodornases) which can be distinguished from one another by column chromatography, electrophoresis and serological methods. These isoenzymes are identified by A, B, C and D, but this is unrelated to the Lancefield classification of Streptococci. Streptococcal DNase B is an antigen which induces the formation of specific antibodies in humans. Knowledge of the concentration of these antibodies in human blood is of diagnostic importance.

Anti-DNase determination (determination of antibodies against streptococcal DNase B) has diagnostic advantages over anti-streptolysin O determination. Especially in skin infections there is rarely an increase in the anti-streptolysin O content, whereas a massive increase in the anti-DNase B titer is observed (J. clin. Invest. (1970) 49, 1405). In acute rheumatic fever, in glomerulonephritis and upper respiratory tract infections there is a pronounced and long-lasting increase in the concentration of antibodies against streptococcal DNase B. Hence there is a need for a means of rapid diagnostic determination of antibodies against streptococcal DNase B.

No straightforward and rapid immunological method for the determination of anti-DNase B has yet been disclosed.

The known enzymatic methods are time-consuming and demand special care or very elaborate apparatus.

In general, the latex agglutination test is known to be a straightforward and rapidly performed method for the detection or the determination of an antigen or antibody. One embodiment comprises addition to a dispersion of latex particles, to which an antibody is bound, of a defined amount of the corresponding antigen and the sample in which the amount of the same antibody which it contains is to be determined.

The binding of DNase antibodies to particles "sensitizes" them for reaction with DNase, and they would react with DNase, with agglutination of the particles. If, however, human serum which is to be tested and which contains antibodies against DNase is mixed with the sensitized particles and DNase, then these antibodies react with the DNase, and there is no agglutination of the particles if the amount of DNase is chosen to be such that it does not exceed the amount of anti-DNase in the serum.

Accordingly, for a determination of antibodies against streptococcal DNase B, use is made of a solution of this enzyme in which the enzyme is sufficiently stable to ensure that the duration of utilizability of a corresponding test system is sufficient for practical purposes. This arises because this enzyme loses activity in aqueous solution. Hence, in the known anti-DNase B test methods the DNase B is lyophilized, and an enzyme solution obtained by dissolving such a lyophilisate in an aqueous solution must, according to the manufacturers, be used within about 48 hours.

Additives to the DNase enzyme preparation which have been described are $MgCl_2$, $MgSO_4$, $CaCl_2$ and bovine serum albumin in imidazole.HCl buffer solution, pH 8, and gelatin and polyhydroxy compounds such as dextran or sugars.

It has now been found that a stable DNase B solution with full immunological activity can be prepared by addition of a protease inhibitor, preferably a benzamidinium salt.

Thus the invention relates to a latex agglutination method for the detection of antibodies against streptococcal deoxyribonuclease B in which antibodies directed against streptococcal deoxyribonuclease B are located on the particles of a dispersion, and this dispersion is mixed with a streptococcal DNase B solution and with the sample which is to be determined, which comprises the streptococcal DNase solution containing a protease inhibitor, and the streptococcal DNase having been, where appropriate, crosslinked.

This method permits straightforward and rapid determination of antibodies against streptococcal deoxyribonuclease B in aqueous solution with high specificity, and with the reagent having a duration of utilizability which is better than that of the state of the art.

The protease inhibitor is preferably a benzamidinium salt, particularly preferably the hydrochloride.

The invention also relates to an agglutination reagent composed of a suspension or dispersion of particles, preferably a dispersion of polystyrene latex particles, on which are located DNase B antibodies, and of a stabilized aqueous solution of streptococcal DNase B which is, where appropriate, crosslinked.

To prepare such particles loaded with DNase antibodies, animals, preferably rabbits, are immunized with streptococcal DNase B, and antibodies against this DNase are obtained. These antibodies against streptococcal DNase B are bound to suspended particles (latex, suspended erythrocytes) by contacting a solution of these DNase antibodies with the particles.

Streptococcal DNase B preparations suitable for immunization can be prepared by methods known per se, for example by precipitating DNase B, which has been obtained by fermentation, with ammonium sulfate, dialysis of the residue, and purification by column chromatographic methods or electrofocusing. It is then possible to use such a purified DNase B enzyme preparation to obtain antibodies against DNase B in mammals. Any non-specific constituents which are present can be removed by known methods (immuno-absorption). However, monoclonal antibodies which can be prepared by known methods ought also to be suitable.

Particularly suitable particle suspensions are polymer latices, preferably polystyrene dispersions.

Examples which may be mentioned are: latices from homopolymers and copolymers of styrene or its derivatives such as methylstyrene, ethylstyrene or chlorostyrene, or acrylic acid or its esters, such as methyl acrylate or ethyl acrylate, or methacrylic acid or its derivatives, such as ethyl methacrylate, acrylonitrile or acrylamide, of dienes such as butadiene, chloroprene or isoprene, of vinyl chloride, vinylidene chloride or vinyl acetate.

Of these, the latices of the homopolymers or copolymers of styrene, acrylic acid or methyl methacrylate are advantageously used.

Preferred latices have a particle size of about 0.05 to 1 μm, in particular particles of a size from 0.1 to 0.6 μm.

Stabilized erythrocytes can also be used as carriers.

The particles can be loaded with the antibody in the following manner: a gamma-globulin fraction is precipitated in a customary manner from an antiserum containing the antibody, and is dissolved in a concentration of 0.01 to 4 g/100 ml in a 0.005 to 0.2 molar buffer with a pH of 7 to 9. The buffer which is expediently used is a glycine/NaCl, phosphate, imidazole or borate buffer. A 0.15 mol/l glycine/NaCl buffer solution of pH 8.2 is preferred. A suspension of latex particles with a concentration of 0.1 to 10 g/100 ml is added to the gamma-globulin solution, and the mixture is left to stand, or is stirred, at room temperature for 1 to 20 hours or at 35 to 56° C. for 0.5 to 16 hours. The suspension is then centrifuged in order to remove unbound protein.

The antibody can also be covalently bonded by known methods to the particle material.

The latex particles loaded with antibodies are suspended in a buffer solution, preferably a glycine/sodium chloride or imidazole buffer solution, in particular a 0.1 to 0.3 molar glycine/NaCl buffer solution which can contain up to 3 g/100 ml, preferably 1 to 2 g/100 ml, human or bovine serum albumin, so that, preferably, a concentration of 0.6 to 1.2 g of latex in 100 ml of suspension is obtained.

A stabilized streptococcal DNase solution suitable for the reagent according to the invention contains 0.1–1 mg/ml DNase B, up to 2 g/100 ml of a degraded and cross-linked gelatin, up to 3 g/100 ml benzamidinium chloride or aprotinin, and 0–5 g/100 ml of a magnesium salt.

A stabilized streptococcal DNase solution suitable for the reagent according to the invention can be obtained by addition of 0.1–2 g/100 ml benzamidinium hydrochloride, 0.1–1.5 g/100 ml $MgSO_4$, 0.5–2 g/100 ml albumin and/ or 0–1 g/100 ml of a gelatin derivative which can be obtained by limited hydrolysis of gelatin and crosslinking of the fragments with a bifunctional reagent, for example polygeline, and, where appropriate, 0.1 g/100 ml of a preservative such as sodium azide, to an aqueous solution containing 1–100 mg/100 ml streptococcal DNase B.

If the DNase B has previously been crosslinked with a bifunctional reagent, for example glutaraldehyde, the solution has particularly advantageous stability properties, and the agglutination of the latex particles results in more readily visible agglutination patterns in the test.

The concentration of the enzyme is adjusted so that it is about 2,500 U of enzymatic activity per ml, or 50 U per test. The streptococcal DNase B does not need to be purified by elaborate physical methods. Ammonium or sodium sulfate precipitation and dialysis of the enzyme suffice.

The examples which follow illustrate the invention.

EXAMPLE 1

Loading of the particles with anti-DNase B 45 ml of a gamma-globulin fraction, containing 50 g/l, from rabbit anti-streptococcal DNase B serum were mixed with 500 ml of polystyrene latex (100 g/l solids) with a particle size of 0.2–0.3 μ, in 0.15 molar glycine/NaCl buffer solution, pH 8.2, and the mixture was incubated in a water-bath at 56° C. for 3 hours. The solid was isolated by centrifugation at about 14,600 xg three times, decanting and washing by resuspension in 1500–1700 ml portions of glycine/NaCl buffer, and was then resuspended in 4500 ml of a solution of 10 g/l bovine serum albumin in glycine/NaCl buffer solution.

Preparation of a streptococcal DNase B solution 500 mg of streptococcal DNase B solution were dissolved in 100 ml of phosphate-buffered saline (PBS), pH 7.1, and 1 g of benzamidinium chloride and 2 g of $MgSO_4$ were added. 10 g of polygeline and 2 g of albumin in 100 ml of phosphate-buffered saline, pH 7.1, were added, and the volume was made up to 1,000 ml with PBS. Then 0.5 g of sodium azide was added to the solution.

Procedure for detecting anti-DNase B in serum 1 drop (50 μl) of human serum for testing was placed on one field of a test plate, and 25 μl of stabilized streptococcal DNase B solution and 25 μl of anti-streptococcal DNase B-latex were added. After thorough mixing with a stirring rod, the test plate was agitated by rotation, and agglutination was checked after five minutes.

The table which follows demonstrates the reliability of the method:

| Serum No. | Anti-DNase B toluidine blue method (U/ml) | Latex test according to the invention |
|---|---|---|
| 1 | 50 | − |
| 2 | 300 | + |
| 3 | 600 | + |
| 4 | 600 | + |
| 5 | 150 | − |
| 6 | 150 | − |
| 7 | 1200 | + |
| 8 | 75 | − |
| 9 | 50 | − |
| 10 | 50 | − |

+ denotes no agglutination; − agglutination

Stability tests for up to one year showed that the streptococcal DNase B solution which was used was stable for at least this period.

EXAMPLE 2

An anti-DNase latex prepared as in Example 1 was used in the test with a streptococcal DNase B preparation which had been prepared in the following manner: 100 mg of enzyme preparation were dissolved, together with 2.5 g of magnesium sulfate, in 1,000 ml of isotonic saline, and 10 g of polygeline, 2 g of benzamidinium hydrochloride and 1 g of sodium azide were added. The activity of the solution was adjusted by dilution to about 2500 U/ml.

EXAMPLE 3

20 ml of a gamma-globulin fraction, containing 45 g/l, from rabbit anti-streptococcal DNase B serum were mixed with 150 ml of polystyrene latex (100 g/l solids) with a particle size of 0.4 μ, in 0.15 molar glycine/NaCl buffer, pH 8.2, and the mixture was incubated in a water-bath at 37° C. for 16 hours. The solid was isolated by centrifugation at about 14,600 xg, washing by decantation and resuspension in 1500 ml portions of glycine/NaCl buffer solution, and was then resuspended in 1500 ml of a solution of 10 g/l human albumin in glycine/NaCl buffer solution.

100 mg of streptococcal DNase B were dissolved in 100 ml of phosphate buffer solution, pH 7.5–8, and 0.5 ml of a 2 g/100 ml glutaraldehyde solution was added. After the solution had been stirred at 4° C. for 5 hours, 2.5 g of magnesium sulfate which had been dissolved in 200 ml of distilled water, 10 g of polygeline, 2 g of benzamidinium chloride and 1 g of sodium azide were added. The volume of the solution was made up to about 1 l, so that each ml contained about 2500 E/ml DNase B activity.

The solution thus prepared was used in the test. This entailed 1 part of undiluted patient's serum being mixed with 0.5 part of DNase B preparation (for example 100 μl of patient's serum + 50 μl of DNase B preparation). The serum sample was then left to stand at room temperature for 5-10 min. 50 μl of the serum/enzyme preparation were placed on one field of a test plate, and 25 μl of DNase B-latex were added. After thorough mixing with a stirring rod, the test plate was agitated by rotation for 5 minutes.

EXAMPLE 4

Latex reagent prepared as in Example 1 was used in the test with a streptococcal DNase B preparation which had been prepared in the following manner:

1,000 mg of enzyme preparation were dissolved in 1,000 ml of phosphate buffer solution, pH 7.5, which contained 2.5 g of magnesium sulfate, and 1.5 ml of a solution of 2 g of glutaraldehyde in 100 ml of water were added. After the solution had been stirred at 4° C. for 5 hours, turbidity and flocculation were removed by filtration or centrifugation. 10 g of polygeline and 2 g of benzamidinium hydrochloride were added to the solution, and then 1 g of sodium azide was added. The activity of the solution was adjusted, by dilution with isotonic saline, to 2500 U/ml by comparison with a standard. The solution prepared in this way was used in the test as described under 1, with more than 90% agreement with the toluidine blue method being obtained on a relatively large collection of subjects' sera (500 sera).

I claim:

1. An indirect latex agglutination method for the detection of antibodies against streptococcal deoxyribonuclease B contained in a liquid, said method comprising:
   (a) contacting a sample of said liquid to be analyzed and a suspension or dispersion of latex particles carrying antibodies directed against streptococcal deoxyribonuclease B,
   (b) adding a stabilized streptococcal deoxyribonuclease B preparation comprising
      (i) streptococcal deoxyribonuclease B, and
      (ii) a protease inhibitor,
   (c) mixing said solutions thoroughly; and
   (d) observing any visible agglutination pattern, whereby the presence of anti-streptococcal deoxyribonuclease B in said sample is indicated by a non-agglutination of said particles.

2. The method as claimed in claim 1, wherein the protease inhibitor is a benzamidinium salt.

3. The method as claimed in claim 1, wherein the stabilized deoxyribonuclease B preparation contains 0.1-1 mg/ml deoxyribonuclease B, up to 2 g/100 ml of a polygeline gelatin derivative, which is obtained by a limited hydrolysis and crosslinking of the fragments, up to 3 g/100 ml benzamidinium chloride, and 0-5 g/100 ml of a magnesium salt.

4. The method as claimed in claim 1, wherein the stabilized streptococcal deoxyribonuclease B preparation contains up to 3 g/100 ml aprotinin, up to 2 g/100 ml of a polygeline gelatin derivative, which is obtained by a limited hydrolysis and crosslinking of the fragments, and 0-5 g/100 ml of a magnesium salt.

5. The method as claimed in claim 1, wherein the streptococcal deoxyribonuclease B preparation contains streptococcal deoxyribonuclease B which has been treated with a crosslinking agent.

6. The method as claimed in claim 1, wherein the latex particles are polystyrene particles.

7. The method as claimed in claim 1, wherein the antibodies carried by the latex particles are from a mammal.

8. The method as claimed in claim 1, wherein the antibodies carried by the latex particles are from a rabbit.

9. An agglutination test system comprising in two separate containers two reagents, wherein said first reagent is a suspension or dispersion of particles on which are located deoxyribonuclease B antibodies, and wherein said second reagent is an aqueous solution of streptococcal deoxyribonuclease B which contains a protease inhibitor.

10. A reagent as claimed in claim 9, wherein the particles are polystyrene particles.

11. An indirect latex agglutination method for the detection of antibodies against streptococcal deoxyribonuclease B contained in a liquid, said method comprising:
    (a) contacting a sample of said liquid to be analyzed and a suspension or dispersion of latex particles carrying antibodies directed against streptococcal deoxyribonuclease B;
    (b) adding a stabilized streptococcal deoxyribonuclease B preparation comprising
       (i) cross-linked streptococcal deoxyribonuclease B, and
       (ii) a protease inhibitor;
    (c) mixing said solutions thoroughly; and
    (d) observing any visible agglutination pattern, whereby the presence of the anti-streptococcal deoxyribonuclease B in said sample is indicated by non-agglutination of said particles.

* * * * *